United States Patent
Beard et al.

[11] 3,965,113
[45] June 22, 1976

[54] 5(6)-BENZENE RING SUBSTITUTED BENZIMIDAZOLE-2-CARBAMATE DERIVATIVES HAVING ANTHELMINTIC ACTIVITY

[75] Inventors: Colin C. Beard, Palo Alto; John A. Edwards, Los Altos; John H. Fried, Palo Alto, all of Calif.

[73] Assignee: Syntex (U.S.A.) Inc., Palo Alto, Calif.

[22] Filed: Nov. 21, 1973

[21] Appl. No.: 417,968

Related U.S. Application Data

[63] Continuation-in-part of Ser. No. 319,299, Dec. 29, 1972, abandoned.

[52] U.S. Cl.............................. 260/309.2; 424/273
[51] Int. Cl.².......................................... C07D 235/32
[58] Field of Search.................................. 260/309.2

[56] References Cited
UNITED STATES PATENTS

| | | | |
|---|---|---|---|
| 3,401,171 | 9/1968 | Craig et al. | 260/309.2 |
| 3,480,642 | 11/1969 | Stedman | 260/309.2 |
| 3,652,580 | 3/1972 | Janiak et al. | 260/309.2 |
| 3,714,180 | 1/1973 | Haugwitz et al. | 260/309.2 |
| 3,720,686 | 3/1973 | Narayanan et al. | 260/309.2 |

*Primary Examiner*—G. Thomas Todd
*Attorney, Agent, or Firm*—Joseph I. Hirsch; William B. Walker

[57] ABSTRACT

Benzene ring substituted benzimidazole-2-carbamate derivatives represented by the formula:

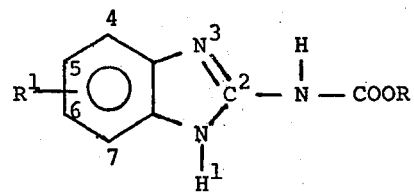

where R is a lower alkyl group having 1 to 4 carbon atoms; $R^1$ is $-SR^5$ or $-OR^5$; and $R^5$ is aryl. The $R^1$ substitution is at the 5(6)-position.

The compounds are useful as pesticides, particularly as anthelmintic and antifungal agents.

7 Claims, No Drawings

5(6)-BENZENE RING SUBSTITUTED BENZIMIDAZOLE-2-CARBAMATE DERIVATIVES HAVING ANTHELMINTIC ACTIVITY

REFERENCE TO PARENT APPLICATION

This application is a continuation-in-part application of application Ser. No. 319,299, filed Dec. 29, 1972 now abandoned.

FIELD OF THE INVENTION

This invention relates to novel chemical compounds. More particularly, this invention relates to novel anthelmintically active benzimidazole-2-carbamate derivatives wherein the benzene ring is substituted at the 5(6)-position.

BACKGROUND OF THE INVENTION

Anthelmintically active benzimidazole-2-carbamate derivatives either unsubstituted at the 5(6)-position or substituted with different substituents than those described and claimed herein are known in this art (for example, see U.S. Pat. Nos. 3,480,642; 3,573,321; 3,574,845; 3,578,676; and 3,595,870). Related fungicidal compounds are also shown in U.S. Pat. Nos. 2,933,504 and 3,010,968.

SUMMARY OF THE INVENTION

The novel benzene ring substituted benzimidazole-2-carbamate derivatives of the present invention can be represented by the following formula:

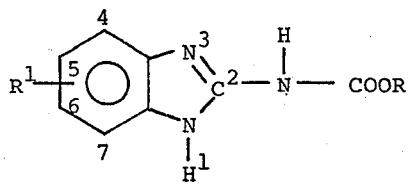

where R is a lower alkyl group having 1 to 4 carbon atoms; $R^1$ is $-SR^5$ or $-OR^5$; and $R^5$ is aryl. The $R^1$ substitution is at the 5(6)-position.

The hydrogen on the nitrogen at the 1-position can be replaced with substituents which do not adversely affect the anthelmintic and/or antifungal properties of the basic compound, including N-alkylcarbamoyl, N,N-dialkylcarbamoyl, N-alkoxycarbonylcarbamoyl, cyano, trichloromethylthio, alkylthio, phenylthio, nitrophenylthio, alkylsulfinyl, phenylsulfinyl, acyl, alkoxycarbonyl, benzoyl, alkoxycarbonylalkylcarbonyl, alkyl, alkenyl, benzyl, alkoxyalkyl, alkoxycarbonylalkyl, carboxyalkyl, hydroxy, and conventional esters and ethers thereof, etc.

As used in this specification and claims, the term "lower alkyl" refers to both straight and branched chain alkyl groups having either a total of from 1 through 4 carbon atoms or from 1 through 6 carbon atoms, and thus includes primary, secondary and tertiary alkyl groups. Typical lower alkyls include, for example, methyl, ethyl, n-propyl, isopropyl, n-butyl, isobutyl, t-butyl, n-amyl, n-hexyl and the like.

The term "aryl" refers to an aromatic hydrocarbon group, such as phenyl or naphthyl. The aryl group can be optionally substituted with one or more lower alkyl, alkoxy, halo, nitro, cyano hydroxy, thiocyanato, isothiocyanato, trifluoromethyl, alkylthio, alkylsulfinyl, alkylsulfonyl, acyl or acylamino where the acyl portion has 1 to 6 carbon atoms, $-SO_2NR^3R^4$ or $-N(R^3)SO_2R^4$ radicals; where $R^3$ and $R^4$ are independently hydrogen or lower alkyl having 1 to 6 carbon atoms. The term "alkoxy" refers to the group having the formula RO— wherein R is a lower alkyl as defined above. Typical alkoxy groups include, for example, methoxy, ethoxy, t-butoxy and the like. The term "halo" refers to iodo, bromo, chloro and fluoro groups. The term "acyl" refers to acyl groups derived from carboxylic acids having from 1 through 6 carbon atoms such as acetyl, propionyl, butyryl, valeryl, isovaleryl, hexanoyl and the like.

The terms "alkylthio", "alkylsulfinyl", or "alkylsulfonyl" refer to those groups having the formula RS—,

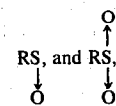

respectively, wherein R is a lower alkyl as defined above.

The compounds of the present invention, and the non-toxic salts thereof formed with pharmaceutically acceptable inorganic or organic acids, possess broad spectrum activity against parasites of mammals, including both mature and immature parasitic forms, as represented for example, by the genera Trichostronglylus, Haemonchus, Ostertagia, Cooperia, Nematodirus, and Stronglyoides, and specifically, for example against *Nematospiroides dubius*, *Hymenolepis Nana*, *Syphacia obvelata*, and/or *Aspiculuris tetraptera*. In particular, these compounds are found to exhibit high activity against various helminthic infections of the intestinal tract of economically important animals, coupled with low systemic toxicity to the host animal.

The compounds of the present invention are also useful as antifungal agents, particularly as systemic fungicides for controlling fungal diseases of plants of economic importance.

In addition to the stated anthelminthic and antifungal properties, certain compounds of the present invention are also useful as intermediates in the preparation of further compounds of this invention. For example, the 5(6)-thio compounds can be prepared and then utilized as starting materials for the preparation of the corresponding 5(6)-sulfinyl or 5(6)-sulfonyl compounds which also are anthelmintically-active.

Where the compound has a basic moiety, the term non-toxic salts as used herein refers to those pharmaceutically acceptable salts of the compounds of this invention which do not adversely affect the antifungal or anthelmintic properties of the basic compound, such as those salts conventionally used in the art. Such non-toxic salts include, for example, salts of inorganic acids such as, for example, sulfuric, sulfonic, sulfamic, nitric, phosphoric hydrochloric acids and the like, and salts of organic acids such as, for example, acetic, citric, lactic, palmitic, tartaric, succinic, maleic, benzoic acids and the like. Where the compound has an acidic moiety, the non-toxic salts include cation salts, such as, for example, the salts of sodium, potassium, ammonium, and the like.

The amount of the compound to be administered will depend upon the actual compound utilized, and upon the weight of the animal being treated. In general, however, the daily dosage level will usually be between about 5 mg/kg and 100 mg/kg of body weight of the animal being treated. The active ingredient is adapted to be administered to the animal by mixing it with the diet of the animal, as with a feed mix, or formulating it with a non-toxic carrier to give anthelmintic compositions. The carrier may be an orally ingestible container for the active ingredient such as, for example, a gelatin capsule, or it may be an excipient of the kind normally used in medicaments of this character, including maize starch, terra alba, lactose, sucrose, calcium phosphate, gelatin, stearic acid, agar, pectin or the like. Examples of suitable liquid carriers are peanut oil, sesame oil and water.

A wide variety of pharmaceutical forms can be employed in those cases wherein the medicament is not admixed with the feed. Thus, if a solid carrier is used, the compound can be administered in tablet or capsule form. If a liquid carrier is used, the medicament may be in the form of a soft gelatin capsule or in a liquid suspension.

In general, the compounds of the present invention can be prepared from benzene starting compounds having nitro and amino or acylamino (for example, acetamido) substituents at adjacent positions on the benzene nucleus (e.g., the 1- and 2-positions), and the desired $R^1$ moiety (or a moiety which can be reacted to give the desired $R^1$ moiety) at the 4- or 5-position of the benzene nucleus (i.e., at what will be the 5- or 6-position of the benzimidazole compound to be prepared). The nitro group is reduced to an amino group to afford a benzene derivative having amino groups at the 1- and 2-positions. The diamino compound is then reacted with a 1,3-bis(alkoxy-carbonyl)-S-alkylisothiourea to give the corresponding 5(6)-substituted benzimidazole 2-carbamate derivative.

The functional moiety at the 4- or 5-position of the benzene starting material can be, for example, chloro which can be reacted with a substituted or unsubstituted aryl mercaptan to afford the corresponding arylthio compound, or it can be a phenoxy group. The arylthio group, in turn, can be converted, by known reactions, to an arylsulfinyl or an arylsulfonyl group (in which case the arylthio compounds of this invention have utility as intermediates). The chloro and phenoxy starting materials are compounds previously reported in the literature.

A reaction sequence particularly useful for preparing substituted or unsubstituted 5(6)-arylthio or aryloxy benzimidazole 2-carbamates is as follows:

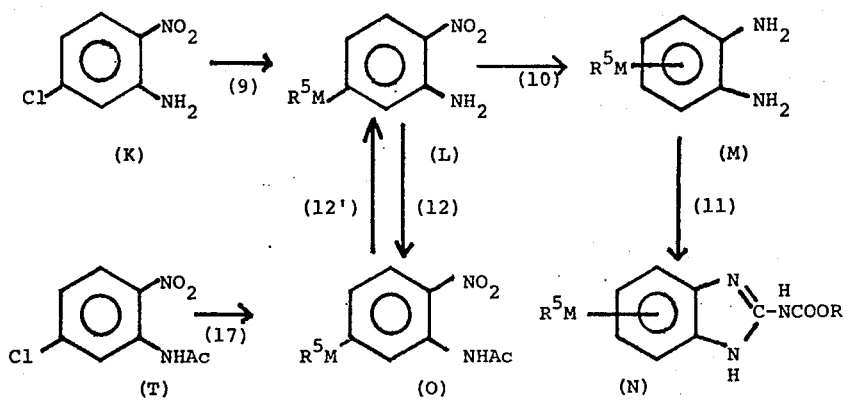

where $R^5$ is as defined above, and M is either O or S.

A suitable alternate reaction sequence for preparing unsubstituted phenoxy compounds (i.e., wherein $R^5$ is phenyl) is as follows:

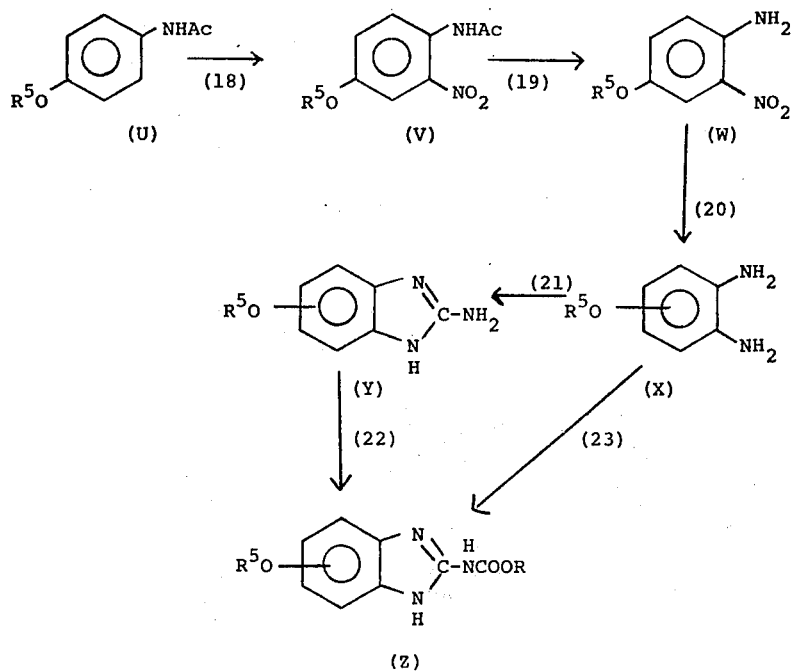

Suitable starting materials include, for example, 2-amino-4-chloro-1-nitrobenzene, 2-acetamido-4-chloro-1-nitrobenzene, and 1-acetamido-4-phenoxybenzene.

When 2-amino-4-chloro-1-nitrobenzene (ie, compound K) or 2-acetamido-4-chloro-1-nitrobenzene is utilized as a starting material, it can be converted to the corresponding substituted or unsubstituted 4-phenylthio compound, as represented by reaction 9 above, by the reaction thereof with an appropriate aryl mercaptan, such as phenylmercaptan, p-chlorophenylmercaptan or p-methoxyphenylmercaptan, in an inert solvent, such as dimethylformamide, ethanol, or methanol, in the presence of a suitable inorganic base, such as potassium hydroxide, potassium carbonate, sodium carbonate, sodium hydroxide or sodium hydride. Typically, this reaction is conducted at a temperature from about 20°C. to about 150°C. (i.e., to about the reflux temperature of the solvent material) for about ½ to about 6 hours, using a slight excess (1.5–2 moles) of the mercaptan reactant.

The 2-amino-4-chloro-1-nitrobenzene starting material can be converted to the corresponding phenoxy compound in accordance with the displacement procedure described above wherein the 4-chloro compound is reacted with an aryl mercaptan, except that an aryl alcohol, such as phenol, p-chlorophenol or p-methoxyphenol, is utilized in place of the mercaptan reactant and the reaction time is somewhat longer, generally on the order of about 1 to about 24 hours.

Reduction of the nitro group to an amino group, as exemplified by steps 10 and 20 above, can be effected by a variety of techniques. For example, the nitro group can be catalytically reduced utilizing hydrogen over a palladium/charcoal catalyst. This reaction is conducted in an inert solvent, such as methanol, at a temperature from about 0°C. to 35°C., generally about room temperature, for about ½ to about 2 hours. Other suitable inert solvents include ethyl acetate, acetic acid, and ethanol. This technique is particularly suitable for compounds which contain an aryloxy substituent at the 4- or 5-position of the benzene nucleus.

Another suitable reducing technique is to treat the nitro-containing compound with iron powder and a ferrous salt, such as ferrous sulfate or ferrous chloride, in aqueous methanol at reflux under neutral conditions for about 1 to about 6 hours. Other suitable reaction media include acetic acid or concentrated hydrochloric acid, and other suitable metals, such as zinc. It is desirable to add the iron powder in distinct portions (as opposed to all at one time), and to carefully monitor the reactants and reaction conditions to insure that the reaction proceeds as desired. This technique is suitable for starting materials which contain an aryloxy or arylthio substituent.

A reduction technique suitable for use with aryloxy or arylthio substituted compounds is to treat such compounds with stannous chloride in concentrated hydrochloric acid at a temperature in a range from about −20°C. to about 100°C., generally about room temperature, for about ½ to about 6 hours. An excess of the stannous chloride reactant should be utilized, generally about 5 parts (by weight) per unit weight of the starting compound.

The diamino compounds, as exemplified by Compounds M and X above are converted to the corresponding benzimidazole 2-carbamate compounds, for example by reaction steps 11 and 23, respectively, by reacting the diamino compound with a 1,3-bis(alkoxycarbonyl)-S-alkyl-isothiourea, for example 1,3-bis(methoxycarbonyl)-S-methyl-isothiourea or 1,3-bis(ethoxycarbonyl)-S-methyl-isothiourea, in an aqueous alcoholic medium, for example, aq. methanol or aq. ethanol, at from about room temperature to the reflux temperature of the reaction medium for about ½ to about 6 hours. The reaction medium is preferably made acidic to a pH of about 4–6 with, for example, a sufficient amount (e.g., 1–2 moles) of acetic acid. About 1–2 moles, generally about 1.1 moles, of the isothiourea reactant are utilized per mole of the diamino compound.

The conversion of an amino group to an acylamino group, for example, an acetamido group, as exemplified by step 12 above, can be conveniently effected by treatment with an acyl halide, for example acetyl chloride or acetic anhydride, in an inert organic reaction medium which dissolves, or is adjusted to dissolve, the compound being treated. For example, suitable organic reaction media include tetrahydrofuran in the presence of pyridine, acetone, in the presence of base such as potassium hydroxide or potassium carbonate, or pyridine alone. Acetic anhydride can be used as the acylating reactant and can also be utilized as the reaction medium. When so utilized, the acetic anhydride is present in substantial excess, generally in an amount sufficient to dissolve the compound being reacted. The well-known Schotten-Baumann reaction can also be utilized for the above purpose. In such a reaction, the compound being treated is dissolved in an aqueous base, an excess of acetic anhydride is added and the precipitated product collected by filtration. When acetic anhydride is utilized in these reactions, it can be utilized in combinations with an acidic catalyst, such as sulfuric acid or paratoluene-sulfonic acid. These reactions are typically conducted at a temperature from about −30°C. to about room temperature for about ¼ hour to about 24 hours using a slight excess (about 1.5–2 moles) of the acylating agent.

Conversion of an acylamino group, for example, an acetamido group, to an amino group, as exemplified by steps 12' and 19 above, can be effected by treating the acylamino group-containing compound with a strong acid, such as hydrochloric acid, or strong base, such as sodium hydroxide, potassium hydroxide, potassium carbonate, or sodium carbonate in aqueous methanol at about 20°C. to about 100°C. for about ¼ hour to about 24 hours. The selection of either the strong acid or the strong base will depend upon the substituent at the 4- or 5-position of the benzene nucleus; generally, for most substituents disclosed a strong base is utilized; however, the necessary material for a particular substituent or compound can be determined by routine experimentation or will be apparent from the nature and chemical stability of the particular compound involved.

Reaction step 17 above can be conducted as described above with respect to step 9; however, the reaction is preferably conducted in dimethylformide using, eg. 2-acetamido-4-chloro-1-nitrobenzene (i.e., compound T) as the starting material.

1-Acetamido-4-phenoxybenzene (ie, compound U) can be nitrated (step 18) to 1-acetamido-2-nitro-4-phenoxybenzene by the techniques described by Scarborough, J. Chem. Soc. 132, 2361 (1929) or Oesterlin, Monatsh., 57, 31 (1931).

2-Amino-5(6)-phenoxybenzimidazole (ie, compound Y) is prepared, for example via reaction 21, by reacting 1,2-diamino-4(5)-phenoxybenzene with cyanogen bromide or cyanamide in methanol or ethanol at about room temperature to the reflux temperature of the alcoholic reaction medium for about 1 to about 18–24 hours. The product compound is dissolved in pyridine cooled to about −40°C. and treated with an excess of methylchloroformate, held at about −40°C. for about 1 hour and then permitted to rise to room temperature where it is generally held for about 12–18 hours; whereby, as represented by reaction step 22 above, the 5(6)-phenoxy-benzimidazole-2-carbamate is prepared.

Conversion of the arylthio group to the corresponding sulfinyl or sulfonyl group, or conversion of the sulfinyl to the sulfonyl group (ie, utilizing the arylthio compounds of this invention as intermediates in the preparation of other anthelmintically-active compounds), is conveniently effected by treatment with a peracid, such as peracetic acid, perbenzoic acid, metachloroperbenzoic acid, or perphthalic acid, in an inert solvent for the compound being treated. Suitable solvent materials include, for example, methylene chloride or chloroform. If the compound being treated is not soluble in the particular reaction media desired to be utilized, then a co-solvent material, such as acetic acid or methanol, should be utilized in an amount sufficient to dissolve the compound being treated. Typically, the reaction is conducted at a temperature from about −30°C to about room temperature for about ½ hour to about 6 hours. When it is desired to convert the arylthio group to the sulfinyl group, molar quantities are utilized, and reaction conditions are carefully monitored to insure that the reaction does not proceed further than desired. When it is desired to convert the arylthio group to the sulfonyl group, or it is desired to convert the sulfinyl group to the sulfonyl group, an excess of the peracid material, for example, 2 moles of the peracid per mole of the compound being treated, is utilized and the reaction conditions do not have to be as carefully monitored. Optionally, such conversions can also be effected by treatment with periodate in aqueous methanol or aqueous acetonitrile at a temperature in the range of about −20° to about 50°C., for about ½ to about 12 hours.

In each of the process steps, described herein above and below, unless otherwise indicated, the respective intermediate products are preferably separated from the reaction mixture and purified prior to their use as starting materials for the next step in the process. Such separation and purification can be effected by any suitable procedure. For example, typical separation procedures include filtration, extraction, evaporation, and typical purification procedures include crystallization, and both thin-layer and column chromatography. Optimum separation and isolation procedures can be obtained for any given step by routine experimentation as will be apparent to those skilled in this art.

Particular compounds falling within the scope of the present invention can be prepared by selecting an appropriate starting material, for example, from those referred to above, and then selecting particular reaction step or steps, as for example described above, to give the compound desired. Particular reaction step or steps may be conducted in a different order from that specified above since, in certain instances, the particular sequence of steps may not be critical. In view of this disclosure, the preparation of particular compounds, including compounds falling within the scope of the present invention but not particularly described in this specification, will be apparent to those skilled in this art.

Exemplary of the compounds of the present invention, as represented by the structural formula above, are the following illustrative compounds:

5(6)-phenoxy-2-carbomethoxyaminobenzimidazole;
5(6)-o-chlorophenoxy-2-carbomethoxyaminobenzimidazole;
5(6)-m-chlorophenoxy-2-carbomethoxyaminobenzimidazole;
5(6)-p-chlorophenoxy-2-carbomethoxyaminobenzimidazole;
5(6)-o,p-dichlorophenoxy-2-carbomethoxyaminobenzimidazole;
5(6)-m,p-dichlorophenoxy-2-carbomethoxyaminobenzimidazole;
5(6)-p-bromophenoxy-2-carbomethoxyaminobenzimidazole;
5(6)-m-hydroxyphenoxy-2-carbomethoxyaminobenzimidazole;
5(6)-p-methylphenoxy-2-carbomethoxyaminobenzimidazole;
5(6)-m-fluorophenoxy-2-carbomethoxyaminobenzimidazole;
5(6)-p-fluorophenoxy-2-carbomethoxyaminobenzimidazole;
5(6)-p-methoxyphenoxy-2-carbomethoxyaminobenzimidazole;
5(6)-p-methylthiophenoxy-2-carbomethoxyaminobenzimidazole;
5(6)-p-methylsulfinylphenoxy-2-carbomethoxyaminobenzimidazole;
5(6)-p-methylsulfonylphenoxy-2-carbomethoxyaminobenzimidazole;
5(6)-m-trifluoromethylphenoxy-2-carbomethoxyaminobenzimidazole;
5(6) -p-acetylphenoxy-2-carbomethoxyaminobenzimidazole;
5(6)-p-cyanophenoxy-2-carbomethoxyaminobenzimidazole;
5(6)-p-nitrophenoxy-2-carbomethoxyaminobenzimidazole;
5(6)-p-thiocyanatophenoxy-2-carbomethoxyaminobenzimidazole;
5(6)-p-isothiocyanatophenoxy-2-carbomethoxyaminobenzimidazole;
5(6)-p-acetamidophenoxy-2-carbomethoxyaminobenzimidazole;
5(6)-p-aminosulfonylphenoxy-2-carbomethoxyaminobenzimidazole;
5(6)-p-methylsulfonylaminophenoxy-2-carbomethoxyaminobenzimidazole;

5(6)-naphth-2'-yloxy-2-carbomethoxyaminobenzimidazole;
5(6)-phenylthio-2-carbomethoxyaminobenzimidazole;
5(6)-m-chlorophenylthio-2-carbomethoxyaminobenzimidazole;
5(6)-p-chlorophenylthio-2-carbomethoxyaminobenzimidazole;
5(6)-p-fluorophenylthio-2-carbomethoxyaminobenzimidazole;
5(6)-p-methylphenylthio-2-carbomethoxyaminobenzimidazole;
5(6)-p-methoxyphenylthio-2-carbomethoxyaminobenzimidazole;
5(6)-m-methoxyphenylthio-2-carbomethoxyaminobenzimidazole;
5(6)-p-nitrophenylthio-2-carbomethoxyaminobenzimidazole;
5(6)-p-cyanophenylthio-2-carbomethoxyaminobenzimidazole;
5(6)-p-thiocyanatophenylthio-2-carbomethoxyaminobenzimidazole;
5(6)-p-isothiocyanatrophenylthio-2-carbomethoxyaminobenzimidazole;
5(6)-p-trifluoromethylphenylthio-2-carbomethoxyaminobenzimidazole;
5(6)-p-methylthiophenylthio-2-carbomethoxyaminobenzimidazole;
5(6)-p-methylsulfinylphenylthio-2-carbomethoxyaminobenzimidazole;
5(6)-p-methylsulfonylphenylthio-2-carbomethoxyaminobenzimidazole;
5(6)-p-acetylphenylthio-2-carbomethoxyaminobenzimidazole;
5(6)-p-acetamidophenylthio-2-carbomethoxyaminobenzimidazole;
5(6)-p-aminosulfonylphenylthio-2-carbomethoxyaminobenzimidazole;
5(6)-p-methylsulfonylaminophenoxy-2-carbomethoxyaminoenzimidazole;
5(6)-naphth-2'-ylthio-2-carbomethoxyaminobenzimidazole; and the corresponding 2-carbethoxyaminobenzimidazole, 2-carbopropoxyaminobenzimidazole, and 2-carbobutoxyaminobenzimidazole compounds.

DESCRIPTION OF SPECIFIC EMBODIMENTS

The following specific description is given to enable those skilled in this art to more clearly understand and practice the present invention. It should not be considered as a limitation upon the scope of the invention but merely as being illustrative and representative thereof.

PREPARATION 1

175 G. of S-methyl isothiouronium sulfate in 1 liter of water is cooled to 0°C and 162.5 g. of methylchloroformate added, followed by the addition of a solution of 250 g. potassium hydroxide in 750 ml. water at 0° to 5°C. The crude product is extracted into benzene, the benzene dried evaporated. and the residue recrystallized from methanol. 1,3-bi(methoxycarbonyl)-S-methyl isothiourea is thus obtained.

In a similar manner, substituting ethylchloroformate, propylchloroformate and butylchloroformate for the methylchloroformate, 1,3-bis(ethoxycarbonyl)-S-methyl isothiourea, 1,3-bis(propoxycarbonyl)-S-methyl isothiourea, and 1,3-bis(butoxycarbonyl)-S-methyl isothiourea are, respectively, prepared.

PREPARATION 2

2 G. of 1-amino-2-nitro-4-thiocyanatobenzene is mixed with 6 ml. of concentrated hydrochloric acid and the mixture cooled to about −40°C. A solution of 12 g. stannous chloride in 6 ml. concentrated hydrochloric acid is added dropwise and the mixture allowed to warm slowly to room temperature. After 15–20 minutes at 15°–20°C, the product is filtered off and washed with 12 ml. 6N hydrochloric acid. Treatment with 25 ml. of saturated potassium bicarbonate solution and extraction with chloroform gives the free base. Recrystallization from benzene yields 1,2-diamino-4-thiocyanatobenzene.

A solution of 1.3 g. 1,2-diamino-4-thiocyanatobenzene and 1.7 g. 1,3-bis(methoxycarbonyl)-S-methyl isothiourea in 20 ml. ethanol and 20 ml. water is treated with 0.5 ml. acetic acid. The mixture is refluxed for 1½ hours, then cooled and filtered. The solid is recrystallized from methanolchloroform to yield 2-carbomethoxyamino-5(6)-thiocyanatobenzimidazole.

In a similar manner substituting
1,3-bis(ethoxycarbonyl)-S-methyl isothiourea,
1,3-bis(propoxycarbonyl)-S-methyl isothiourea, and
1,3-bis(butoxycarbonyl)-S-methyl isothiourea for the
1,3-bis(methoxycarbonyl)-S-methyl isothiourea,
2-carbethoxyamino-5(6)-thiocyanatobenzene,
2-carbopropoxyamino-5(6)-thiocyanatobenzene, and
2-carbobutoxyamino-5(6)-thiocyanatobenzene are prepared, respectively.

EXAMPLE I

5 G. of 2-amino-4-chloro-1-nitrobenzene is added to a solution of sodium phenyl mercaptide, prepared under nitrogen from 2.53 g. 57% sodium hydride and 6.2 ml. thiophenol in 20 ml. dimethylformamide, with a 10 ml. dimethylformamide rinse. The mixture is stirred under nitrogen for three hours at 20°–30°C and then diluted with water. The crude product is washed with water and hexane, then recrystallized from methanol, yielding 2-amino-4-phenylthio-1-nitrobenzene.

6.0 G. of 2-amino-4-phenylthio-1-nitrobenzene is dissolved in 80 ml. acetic anhydride and treated with a few drops of sulfuric acid. The mixture is left at 20°–30°C for 2 hours then a little sodium acetate added and the solvent removed under vacuum. The residue is treated with water, filtered and recrystallized from methanol yielding 2-acetamido-4-phenylthio-1-nitrobenzene. [This material may also be obtained by reaction of 2-acetamido-4-chloro-1-nitrobenzene with sodium phenylmercaptide essentially as described above for the free amine.]

3.5 G. of 2-amino-4-phenylthio-1-nitrobenzene in 8 ml. conc. hydrochloric acid is treated with a solution of 16 g. of stannous chloride in 8 ml. conc. hydrochloric acid. The mixture is heated for 1 hour on a steam bath, cooled and treated with potassium bicarbonate and chloroform. The mixture is filtered and the chloroform layer evaporated. The residue is triturated with hot cyclohexane yielding 1,2-diamino-4-phenylthiobenzene.

A mixture of 5.0 g. of 1,2-diamino-4-phenylthiobenzene, 4.3 g. of 1,3-bis-methoxycarbonyl-S-methyl isothiourea and 1.2 ml. acetic acid in 100 ml. ethanol and 100 ml. water is refluxed for 4 hours. The mixture is cooled and essentially pure 2-carbomethoxyamino-5(6)-phenylthiobenzimidazole filtered off and washed with methanol. Recrystallization may be effected from methanol-chloroform.

In a similar manner, substituting 1,3-bis-ethoxy-carbonyl-S-methyl isothiourea, 1,3-bis-propoxycarbonyl-S-methyl isothiourea, or 1,3-bis-butoxycarbonyl-S-methyl isothiourea, for the 1,3-bis-methoxycarbonyl-S-methyl isothiourea, the corresponding 2-carbalkoxyamino-5(6)-phenylthiobenzimidazole compounds are prepared, where R is ethyl, propyl or butyl.

EXAMPLE II

A mixture of 4.1 g. potassium carbonate, 3.7 g. p-thiocresol and 5.1 g. 2-amino-4-chloro-1-nitrobenzene in 20 ml. dimethylformamide is stirred under nitrogen for 20 hours at 20°–25°C, water is added and the product filtered off. Recrystallization from methanol gives 2-amino-4-(p-methylphenylthio)-1-nitrobenzene.

3.5 G. of 2-amino-4-(p-methylphenylthio)-1-nitrobenzene in 8 ml. concentrated hydrochloric acid is treated with a solution of 16 g. stannous chloride in 8 ml. concentrated hydrochloric acid in 20 ml. acetic acid. The mixture is heated for 1 hour on a steam bath, cooled and treated with potassium bicarbonate and chloroform. The mixture is filtered and the chloroform layer evaporated. The residue is triturated with hot cyclohexane giving 1,2-diamino-4-(p-methylphenylthio)-benzene.

2.5 G. 1,2-diamino-4-(p-methylphenylthio)-benzene, 2.3 g. 1,3-bis-methoxycarbonyl-S-methyl isothiourea and 0.75 ml. acetic acid is dissolved in 50 ml. ethanol and 50 ml. water and the mixture refluxed for 3 hours. The cooled mixture is filtered giving 2-carbomethoxyamino-5(6)-(p-methylphenylthio)-benzimidazole, which may be recrystallized from chloroform-methanol.

In a similar manner using p-chlorophenyl mercaptide, p-methoxyphenyl mercaptide, m-methoxyphenyl mercaptide, m-chlorophenyl mercaptide, and p-fluorophenyl mercaptide, in place of the p-thiocresol, 2-carbomethoxyamino-5(6)- p-chlorophenylthiobenzimidazole, 2-carbomethoxyamino-5(6)-p-methoxyphenylthiobenzimidazole, 2-carbomethoxyamino-5(6)-m-methoxyphenylthiobenzimidazole, 2-carbomethoxyamino-5(6)-m-chlorophenylthiobenzimidazole, and 2-carbomethoxyamino-5(6)-fluorophenylthiobenzimidazole, respectively, are prepared.

Also in a similar manner, using any of the 1,2-diamino compounds prepared above in this Example and substituting 1,3-bis-ethoxycarbonyl-S-methyl isothiourea, 1,3-bis propoxycarbonyl-S-methyl isothiourea, or 1,3-bis-butoxycarbonyl-S-methyl isothiourea for 1,3-bis-methoxycarbonyl-S-methyl isothiourea, the corresponding 5(6)-p-methylphenylthio-, 5(6)-p-chlorophenylthio-, 5(6)-p-methoxyphenylthio-, 5(6)-m-methoxyphenylthio-, 5(6)-m-chlorophenylthio- and 5(6)-p-fluorophenylthio-2-carbalkoxyaminobenzimidazole compounds are prepared, where R is ethyl, propyl or butyl.

1.88 G. 2-carbomethoxyamino-5(6)-(p-methylphenylthio)-benzimidazole is dissolved in a mixture of 150 ml. acetic acid and 150 ml. chloroform. A solution of 1.22 g. metachloro-perbenzoic acid in 20 ml. chloroform is added at −15° to −10°C, then the mixture is allowed to warm slowly to 20°–25°C. After 6 hours, the solvent is removed under vacuum at 20°–30°C and the residue treated with sodium bicarbonate solution. The product is filtered off and recrystallization from methanol-chloroform gives 2-carbomethoxyamino-5(6)-(p-methylphenylsulfinyl)-benzimidazole.

EXAMPLE III

In similar manner to the procedure of the first three paragraphs and the last paragraph of Example II, substituting 2-mercaptonaphthalene for the p-thiocresol, there is obtained 5(6)-naphtha-2′-ylthio-2-carbomethoxyaminobenzimidazole, and 5(6)-naphth-2′-ylsulfinyl-2-carbomethoxyaminobenzimdazole, and the corresponding 2-carbalkoxyaminobenzimidazole compounds where R is ethyl, propyl or butyl.

EXAMPLE IV 1.26 G. of 57% sodium hydride in oil is washed under nitrogen with pentane by decantation. 15 Ml. of dimethylformamide is added, then 3.9 g. of p-chlorophenol followed by a rinse with 5 ml. of dimethylformamide. 2.5 G. of 2-amino-4-chloro-1-nitrobenzene is added to the solution which is then heated at 130°–135°C for 5 hours. Water is added and the product filtered off. Recrystallization from methanol gives 2-amino-4-(p-chlorophenoxy)-1-nitrobenzene.

1.2 G. of 2-amino-4-(p-chlorophenoxy)-1-nitrobenzene in 3 ml. concentrated hydrochloric acid is treated with a solution of 6 g. stannous chloride in 6 ml. concentrated hydrochloric acid on the steam bath for 5 minutes. The mixture is cooled, decanted and the residue washed with 6 ml. 6N hydrochloric acid. The residue is treated with potassium bicarbonate and chloroform, filtered, and the chloroform layer repeated and dried over magnesium sulfate. Evaporation leaves 1,2-diamino-4-(p-chlorophenoxy)-benzene as a gum.

0.8 G. of 1,2-diamino-4-(p-chlorophenoxy)-benzene, 0.7 g. of 1,3-bis-methoxycarbonyl-S-methyl isothiourea and 0.25 ml. acetic acid are dissolved in 10 ml. ethanol plus 10 ml. water and the solution refluxed for 3 hours. The mixture is cooled and 2-carbomethoxyamino-5(6)-(p-chlorophenoxy)benzimidazole filtered off and washed with methanol. Recrystallization may be effected from methanol-chloroform.

In a similar manner, using phenol, p-cresol, o-chlorophenol, m-chlorophenol, o,p-dichlorophenol, m,p-dichlorophenol, m-trifluoromethylphenol, p-bromophenol, p-fluorophenol, m-fluorophenol, p-acetylphenol, p-cyanophenol, m-hydroxyphenol, and p-methoxyphenol in place of p-chlorophenol, the corresponding 1,2-diamino-4-phenoxy (or substituted phenoxy) benzenes and 2-carbomethoxyamino-5(6)-phenoxy (or substituted phenoxy) benzimidazole compounds are prepared. Using the 1,2-diamino compounds prepared above in this Example, and substituting 1,3-bis-ethoxycarbonyl-S-methyl isothiourea, 1,3-bis-propoxycarbonyl-S-methyl isothiourea, or 1,3-bis-butoxycarbonyl-S-methyl isothiourea for the 1,3-bis-methoxycarbonyl-S-methyl isothiourea, the corresponding 2-carbalkoxyamino-5(6)-phenoxy (or p-substituted phenoxy) benzimidazole compounds are prepared, where R is ethyl, propyl or butyl.

EXAMPLE V 6.0 G. of 1-acetamido-2-nitro-4-phenoxybenzene and 20 ml. sodium hydroxide in methanol is warmed gently until homogeneous, diluted with water and ice, and the methanol evaporated to give 1-amino-2-nitro-4-phenoxybenzene.

4.8 G. of 1-amino-2-nitro-4-phenoxybenzene is hydrogenated in 100 ml. methanol at 1 atmosphere pressure, in the presence of 1 g. of 5% palladized carbon, until the theoretical uptake of hydrogen has occurred. The catalyst is removed by filtration and the filtrate evaporated to give 1,2-diamino-4-phenoxybenzene.

3.1 G. of 1,2-diamino-4-phenoxybenzene in 50 ml. methanol is reacted with 1.05 g. cyanogen bromide at reflux for one hour to give, upon isolation, 2-amino-5(6)-phenoxybenzimidazole.

2.0 G. of methylchloroformate is added to 1.5 g. of 2-amino-5(6)-phenoxybenzimidazole in 40 ml. pyridine cooled to −40°C. The mixture is held at about −40°C for 1 hour, then permitted to rise to room temperature where it is held for 1 hour. The pyridine is evaporated, the residue treated with ether and 2-carbomethoxyamino-5(6)-phenoxybenzimidazole isolated. Purification may be effected by precipitation from 2N hydrochloric acid with ammonium hydroxide.

EXAMPLE VI 0.84 G. of 57% sodium hydride is added to 3.0 g. p-methylthiophenol in 20 ml. dimethylformamide, 4.3 G. 2-acetamido-4-chloro-1-nitrobenzene is added and the mixture heated at 140°–145°C for 5 hours, cooled and treated with water. The crude product is filtered off, washed with water and pentane. Recrystallization from methanol gives 2-acetamido-4-(p-methylthiophenoxy)-1-nitrobenzene.

3.5 G. of 2-acetamido-4-(p-methylthiophenoxy)-1-nitrobenzene is treated on the steam bath with 7 ml. 5N sodium hydroxide and 50 ml. methanol for 1 hour. The mixture is concentrated, diluted with water and the 2-amino-4-(p-methylthiophenoxy)-1-nitrobenzene filtered off. This material is treated in 18 ml. concentrated hydrochloric acid with 18 g. stannous chloride on the steam bath for 5 minutes. The mixture is cooled, decanted and the solid washed with 18 ml. 6N hydrochloric acid. The free base is liberated by treatment with potassium bicarbonate and extracted into chloroform. Evaporation of the chloroform leaves crystalline 1,2-diamino-4-(p-methylthiophenoxy)-benzene.

2.4 G. 1,2-diamino-4-(p-methylthiophenoxy)benzene, 2.2 g. 1,3-bis-methoxycarbonyl-S-methyl isothiourea, 0.8 ml. acetic acid in 30 ml. ethanol and 30 ml. water is refluxed for 4 hours. The cooled mixture is filtered and the product recrystallized from aqueous acetic acid, yielding 2-carbomethoxyamino-5(6)-(p-methylthiophenoxy)benzimidazole.

0.82 G. of 2-carbomethoxyamino-5(6)-(p-methylthiophenoxy)benzimidazole in 75 ml. acetic acid and 75 ml. chloroform is treated at −15° to −10°C with a solution of 0.51 g. meta-chloro-perbenzoic acid in 10 ml. chloroform. The mixture is allowed to warm slowly to room temperature then stripped under vacuum and the residue treated with sodium bicarbonate solution. Filtration yields 2-carbomethoxyamino-5(6)-(p-methylsulfinylphenoxy)benzimidazole, which may be recrystallized from methanol-chloroform.

0.6 G. of 2-carbomethoxyamino-5(6)-(p-methylthiophenoxy(benzimidazole in 30 ml. acetic acid is treated at 20°–25°C with 1.5 ml. of 40% peracetic acid. The mixture is left for 16 hours, then stripped under vacuum. The residue is treated with sodium bicarbonate solution, filtered off and recrystallized from aqueous acetic acid, yielding 2-carbomethoxyamino-5(6)-(p-methylsulfonylphenoxy)benzimidazole.

In a similar manner, substituting p-ethylthiophenol, p-propylthiophenol, p-(i-propylthio)phenol and p-(n-butylthio)phenol in place of the p-methylthiophenol, the corresponding 1,2-diamino-4-(p-alkylthiophenoxy)benzene, 5(6)-(p-alkylthiophenoxy)-2-carbomethoxyamino benzimidazole, 5(6)-(p-alkylsulfinylphenoxy)-2-carbomethoxyamino benzimidazole and 5(6)-(p-alkylsulfonylphenoxy)-2 carbomethoxyamino benzimidazole compounds are prepared.

Also in a similar manner, reacting the 1,2-diamino-4-(p-alkylthiophenoxy)benzenes so produced with 1,3-bis-ethoxycarbonyl-S-methyl isothiourea, 1,3-bis-propoxycarbonyl-S-methyl isothiourea or 1,3-bis-butoxycarbonyl-S-methyl isothiourea in place of the 1,3-bis-methoxycarbonyl-S-methyl isothiourea, the corresponding 5(6)-(p-alkylthiophenoxy)-2-carbalkoxyamino benzimidazole, 5(6)-(p-alkylsulfinylphenoxy)-2-carbalkoxyamino benzimidazole and 5(6)-(p-alkylsulfonylphenoxy)-2-carbalkoxyamino benzimidazole compounds are produced, where the alkyl portion of the carbalkoxyamino group is either ethyl, propyl or butyl.

EXAMPLE VII

In a similar manner to the procedure of Example IV substituting 2-hydroxynaphthalene for the p-chlorophenol, there is obtained 5(6)-naphtha-2'-yloxy-2-carbomethoxybenzimidazole, and the corresponding 2-carbalkoxyaminobenzimidazole compounds where R is ethyl, propyl or butyl.

In certain of the Examples above, specific reaction sequences have been extended, in a general sense, to the preparation of other similar and related compounds. It should be understood, however, that with respect to any compound which has been prepared by the extension of a specific reaction sequence, it may be necessary or desirable to ultilize solvents, reaction media, recrystallization media, reaction times or temperatures, etc., other than the ones given in the specific reaction sequence upon which such extension is based. Additionally, the specific reaction sequence or manner in which particular compounds are to be prepared will depend, inter alia, upon the availability of the necessary starting materials, or the ease in which the desired starting materials can be prepared, and the reactivity thereof. These variations are deemed to be within the skill of those working in this art and will be apparent from a consideration of the particular reactants utilized and/or particular compound desired to be produced.

While the present invention has been described with reference to specific embodiments thereof, it should be understood by those skilled in this art that various changes may be made and equivalents may be substituted without departing from the true spirit and scope of the invention. In addition, many modifications may be made to adapt a particular situation, material or composition of matter, process, process step or steps, or then-present objective to the spirit of this invention without departing from its essential teachings.

What is claimed is:

1. A compound selected from the group of compounds represented by the formula:

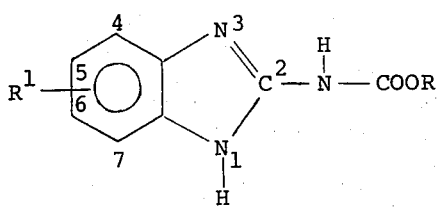

where R is lower alkyl group having 1 to 4 carbon atoms; $R^1$ is —$SR^5$ or —$OR^5$; and $R^5$ is naphthyl optionally substituted with a lower alkyl having 1 to 6 carbon atoms, alkoxy having 1 to 6 carbon atoms, halo, nitro, cyano, hydroxy, thiocyanato, isothiocyanato, trifluoromethyl, alkylthio having 1 to 6 carbon atoms, alkylsulfinyl having 1 to 6 atoms, alkylsulfonyl having 1 to 6 carbon atoms, alkanoyl or alkanoylamino where the alkanoyl portion has 1 to 6 carbon atoms, —$SO_2NR^3R^4$ or —$N(R^3)SO_2R^4$ radical; where $R^3$ and $R^4$ are independently hydrogen or lower alkyl having 1 to 6 carbon atoms; the $R^1$ substitution being at the 5(6)-position; and the non-toxic salts thereof.

2. The compound of claim 1 wherein $R^1$ is —$SR^5$.
3. The compound of claim 1 wherein $R^1$ is —$OR^5$.
4. The compound of claim 1 wherein $R^5$ is naphthyl.
5. The compound of claim 1 wherein said naphthyl group is substituted with a nitro, cyano, thiocyanato, isothiocyanato, alkylthio having 1 to 6 carbon atoms, alkyl-sulfinyl having 1 to 6 carbon atoms, alkylsulfonyl having 1 to 6 carbon atoms, alkanoyl or alkanoylamino where the alkanoyl portion has 1 to 6 carbon atoms, —$SO_2NR^3$ or —$N(R^3)SO_2R^4$ radical; where $R^3$ and $R^4$ are independently hydrogen or lower alkyl having 1 to 6 carbon atoms.

6. A compound selected from the group consisting of:
5(6)-p-methylsulfonylphenoxy-2-carbomethoxyaminobenzimidazole,
5(6)-p-acetylphenoxy-2-carbomethoxyaminobenzimidazole,
5(6)-p-cyanophenoxy-2-carbomethoxyaminobenzimidazole,
5(6)-p-nitrophenoxy-2-carbomethoxyaminobenzimidazole,
5(6)-p-thiocyanatophenoxy-2-carbomethoxyaminobenzimidazole,
5(6)-p-isothiocyanatophenoxy-2-carbomethoxyaminobenzimidazole,
5(6)-p-aminosulfonylphenoxy-2-carbomethoxyaminobenzimidazole,
5(6)-p-methylsulfonylaminophenoxy-2-carbomethoxyaminobenzimidazole,
5(6)-p-acetylphenylthio-2-carbomethoxyaminobenzimidazole,
5(6)-p-acetamidophenylthio-2-carbomethoxyaminobenzimidazole,
5(6)-p-aminosulfonylphenylthio-2-carbomethoxyaminobenzimidazole,
5(6)-p-methylsulfonylaminophenoxy-2-carbomethoxyaminobenzimidazole,
5(6)- naphtha-2'-ylthio-2-carbomethoxyaminobenzimidazole, and the non-toxic salts thereof.

7. The compound of claim 1 wherein said compound is 5(6)-p-acetylphenoxy-2-carbomethoxyaminobenzimidazole.

* * * * *

UNITED STATES PATENT AND TRADEMARK OFFICE
CERTIFICATE OF CORRECTION

PATENT NO. : 3,965,113
DATED : June 22, 1976
INVENTOR(S) : COLIN C. BEARD et al

It is certified that error appears in the above-identified patent and that said Letters Patent are hereby corrected as shown below:

Column 9, line 40, "thoxyaminoenzimidazole;" should read -- thoxyaminobenzimidazole; --. Column 12, line 19, "-carbomethoxyaminobenzimdazole," should read -- -carbomethoxyaminobenzimidazole, --. Claim 6 should read as follows:

6. A compound selected from the group consisting of:
5(6)-p-acetylphenoxy-2-carbomethoxyaminobenzimidazole,
5(6)-p-cyanophenoxy-2-carbomethoxyaminobenzimidazole,
5(6)-p-nitrophenoxy-2-carbomethoxyaminobenzimidazole,
5(6)-p-thiocyanatophenoxy-2-carbomethoxyaminobenzimidazole,
5(6)-p-isothiocyanatophenoxy-2-carbomethoxyaminobenzimidazole,
5(6)-p-acetamidophenoxy-2-carbomethoxyaminobenzimidazole,
5(6)-p-aminosulfonylphenoxy-2-carbomethoxyaminobenzimidazole,
5(6)-p-methoxysulfonylaminophenoxy-2-carbomethoxyaminobenzimidazole,
5(6)-naphth-2'-yloxy-2-carbomethoxyaminobenzimidazole,
5(6)-p-nitrophenylthio-2-carbomethoxyaminobenzimidazole,
5(6)-p-cyanophenylthio-2-carbomethoxyaminobenzimidazole,
5(6)-p-thiocyanatophenylthio-2-carbomethoxyaminobenzimidazole,
5(6)-p-isothiocyanatophenylthio-2-carbomethoxyaminobenzimidazole,
5(6)-p-acetylphenylthio-2-carbomethoxyaminobenzimidazole,
5(6)-p-acetamidophenylthio-2-carbomethoxyaminobenzimidazole,
5(6)-p-aminosulfonylphenylthio-2-carbomethoxyaminobenzimidazole,
5(6)-p-methylsulfonylaminophenoxy-2-carbomethoxyaminobenzimidazole,
5(6)-naphth-2'-ylthio-2-carbomethoxyaminobenzimidazole, and the non-toxic salts thereof.

Signed and Sealed this

Fifth Day of October 1976

[SEAL]

Attest:

RUTH C. MASON
Attesting Officer

C. MARSHALL DANN
Commissioner of Patents and Trademarks